United States Patent [19]
Orton et al.

[11] Patent Number: 5,124,505
[45] Date of Patent: Jun. 23, 1992

[54] CELERY LINES WITH INCREASED STICK YIELD

[75] Inventors: Thomas J. Orton, Aptos, Calif.; Robert J. Whitaker, Burlington, N.J.

[73] Assignee: DNA Plant Technology Corporation, Cinnaminson, N.J.

[21] Appl. No.: 393,626

[22] Filed: Aug. 14, 1989

[51] Int. Cl.$^5$ .......................... A01H 4/00; C12N 5/04
[52] U.S. Cl. ........................ 800/200; 800/DIG. 45; 435/240.4; 435/240.51
[58] Field of Search ........... 435/240.4, 240.49, 240.51; 800/200, DIG. 45

[56] References Cited
PUBLICATIONS

Heath-Pagliuso et al (1988) Theor. Appl. Genet. 75: 446–451.
Karp (Mar. 1989) IAPTC#57: 2–10.
Orton in *Handbook of Plant Cell Culture*, vol. 2, Sharp et al, eds. MacMillan Publishing, NY, 1984, pp. 249–255.
Orton, in Cell Culture and Somatic Cell Genetics of Plants, vol. 3, Vasil, ed., Academic Press, N.Y., 1986, pp. 345–365.
Evans et al., 1984, Amer. J. Bot. 71: 759–774.
Larkin and Scowcroft, 1981, Theor. Appl. Genet. 60: 197–214.
Williams and Collin, 1976, Ann. Bot. 40: 333–338.

*Primary Examiner*—Jacqueline Stone
*Assistant Examiner*—Che Chereskin
*Attorney, Agent, or Firm*—Pennie & Edmonds

[57] ABSTRACT

The present invention provides a method for improving stick yield of a celery line which comprises culturing an explant on a first medium containing at least one auxin to produce callus, culturing the callus on a second medium without growth regulators to produce embryos, growing embryos unit mature plants are obtained and recovering from the mature plants variants exhibiting a stick yield of at least about 25% over stick yield of the parent line. Also provided are novel celery plants, having improved stick yield.

8 Claims, No Drawings

_5,124,505_

CELERY LINES WITH INCREASED STICK YIELD

1. FIELD OF THE INVENTION

The present invention relates to celery lines having improved processing characteristics. In particular, these lines, obtained by somaclonal variation in a progenitor line, exhibit a significant increase in stick length, and therefore, an increased stick yield when the celery is processed for packaging.

2. BACKGROUND OF THE INVENTION

The commercial vegetable crop known as celery is based primarily on the enlarged, succulent petioles of *Apium graveolens*. Although some minor economic value is associated with the leaves and seed of celery, the principle product utilized by the consumer is the petiole stalk. Pascal celery has been domesticated from a wild progenitor to bear at maturity a large number of fleshy, tender, green petioles. These are consumed, both in the U.S. and elsewhere, either as a fresh product, or indirectly in prepared foods such as condensed soups, and dehydrated soup and rice products. Recent consumer interest in having healthful, minimally processed fresh vegetables has given rise to a new category of products which have long shelf-life, but which retain the characteristics of fresh vegetables without additive or extensive processing which may otherwise alter the vegetable characteristics. Such items are being made available under the name "VegiSnax". Among such items are carrot and celery sticks which are precut into 3 inch (7.6 cm) lengths convenient for packaging, and packed according to methods described in U.S. Pat. Nos. 4,711,789, and 4,751,094. The contents of these patents are incorporated herein by reference.

Celery Processing

The goal of celery breeding is the production of good-tasting, consumer acceptable celery with agronomic characteristics which cause them to be well-adapted for their ultimate intended use. Among the considerations which have traditionally concerned breeders are establishing disease resistance, timing of bolting (stem-elongation), petiole shape, color, thickness, succulence and ribbiness, overall height and heart size. Very little is known about the inheritance of variation of many of these traits, however, and therefore, breeding of new cultivars with the desired characteristics is to a large extent intuitive.

For any use which requires significant manipulation of the celery prior to its use by the consumer, the net cost of finishing goods (NCFG) is an important consideration, and therefore, development of varieties with features which contribute to the ease of efficiency of conversion of crop into finished product aid in the reduction of NCFG. In connection with the methods noted above for processing carrots and celery, obtaining maximum yield of cut sticks from petioles is critical to reducing the NCFG to practical levels. Although this is a trait which could conceivably be established through traditional breeding methods of crossing and selection, the danger exists that outcrossing of an elite celery line having all the organoleptic properties necessary for consumer preference, to obtain increased petiole length, will have the effect of altering the already established traits. Since, as already noted, the patterns of inheritance of most of the traits of interest are not well known, it is very difficult to control the outcome of hybridization, so that the resulting plant retains all the organoleptic properties of the elite parent, but has the additional property of increased petiole length. The present invention, by use of somaclonal variation, has now provided celery lines which retain the organoleptic characteristics of an elite pascal celery line, while also exhibiting significantly increased stick yield over the progenitor parent.

Somaclonal Variation

Methods of plant tissue culture have now been used for years as a means of asexual reproduction, enabling a more rapid rate of propagation than is available with traditional vegetative propagation. It is of course expected that the regenerated plants will be exact copies of the plant from which the tissue explant was taken. Early in the history of plant tissue culture, it was noticed that phenotypic variants commonly occurred among regenerated plants. These anomalies were typically dismissed as artifacts of tissue culture, representing "epigenetic" events which were of no value scientifically, except as a curiosity.

It has been more recently recognized that the appearance of such variants is a relatively regular occurrence in certain plants, and this provides a potentially valuable source of genetic variability for use in crop improvement (Larkin and Scowcroft, *Theor. Appl. Gent* 60:197-214, 1981; Evans et al., *Amer. J. Bot.* 71:759-774, 1984). The resulting variants are now referred to as somaclonal variants or somaclones and have been observed in a number of different plant species.

A number of different techniques have been used to induce or favor the production of somaclonal variants (Reisch, "Genetic Variability in Regenerated Plants", in *Handbook of Plant Cell Culture*, Vol. 1, Chap. 25, 1983, McMillan Publishing). Among the manipulations which may be used to encourage variation are long-term culture cycles, protoplast culture cycles, callus culture cycles, explants from specific tissue types, growth on a specific nutrient medium or hormone formulation (for example, U.S. Pat. No. 4,818,699), or the use of specific genotypes known to produce increased amounts of variations. These techniques are not mutually exclusive, and one or more may be combined to achieve the desired level of variation.

The techniques described above have not proven to be reliably applicable to all plants, however. Some species may readily produce somaclonal variants in, for example, a protoplast culture cycle, while other species, even within the same genus, will not. Similarly, there is no way to predict, a priori, the nature of the somaclones which will be produced, until the conditions which induce variation for a particular species have been determined. In essence, unless the species in question has previously been shown to produce somaclones, with any degree of certainty, it is not predictable whether somaclones will be produced, and for what type of characteristics variation will be observed (Orton, in *Gene Manipulation in Plant Improvement*, J. Gustafsen, ed., pp 427-468, Plenum Press, NY, 1984).

Somaclonal Variation in Celery

Genetic variability in tissue culture of celery has previously been observed (see Orton in *Cell Culture and Somatic Cell Genetics of Plants*, Vol. 3, Vasil, ed., pp. 345-365, Academic Press, N.Y., 1986). A substantial amount of variability in chromosome number has been observed among celery cells in a single culture; this may or may not have an effect of the normal regeneration of the cultures, and is variably reflected in the regenerated plants themselves. Some variation in isozyme markers has also been observed.

With regard to phenotypic variation, it was originally believed that culture-derived celery plants were highly stable, and that no variation occurred (Williams and Collin, *Ann. Bot.* (London) 40:333-338, 1976). However, it was later noted that many regenerated celery plants had both masked recessive mutations and other exhibiting complicated inheritance (Orton, ibid). Among the mutations observed in such somaclones are frilly leaf disease resistance, and supernumerary chromatin (Heath-Pagliuso et al., *Theoret. Appl. Genet.* 75:446-451, 1988; Orton et al. *Plant Cell, tissue, and Organ Culture* 4:159, 1985). However, to date, there have been no reports on somaclonal variants exhibiting heritable changes in plant processing characteristics or "architecture", i.e., plant height, shape, etc.

3 SUMMARY OF THE INVENTION

The present invention provides a method for producing novel celery lines which have improved architectural characteristics. More specifically, the method provides a means for obtaining celery lines which have a stick yield which is increased at least 25% over the parental line from which it was derived. These lines have been produced by subjecting elite celery parent lines, having superior organoleptic properties, to a program of somaclonal variation, and selecting those variants having increased petiole length.

The method requires culturing an explant of a selected parent line on a first culture medium comprising an effective amount of at least on auxin until callus is obtained; culturing the callus on a second culture medium which contains no growth regulations until embryos are obtained, continuing culture of embryos until plantlets are obtained, allowing plantlets to develop into mature plants, and recovering from the mature plants variants exhibiting an increase in stick yield of at least 25% over the parent line.

The invention also provides novel variant celery lines with improved stick yield. In a preferred embodiment, the variant line DNAP-331 provides the organoleptic properties of a Tall Utah variety but with superior stick yield. Celery seed producing plants exemplifying the present invention have been deposited with the American Type Culture Collection under accession number ATCC 40621.

4. DETAILED DESCRIPTION OF THE INVENTION

Variant Production

The initial investigations were based upon a program of somaclonal variation on a pascal celery. The celery was cultured according to the method described by Orton (in Vasil (ed.), *Cell Culture and Somatic Cell Genetics of Plants,* Vol. 3., Academic Press, P. 345-366).

As noted above, somaclonal variation can be induced by placing a tissue explant into an appropriate growth medium. In the case of celery, the tissue explant is usually petiole or leaf, but axial buds or young embryo tissue may also be employed. Complete surface sterilization of the tissue is usually performed prior to culture to prevent growth of contaminating microorganisms, and then rinsed two or three times with sterile distilled water. Other methods of sterilization will also be recognized by those skilled in the art.

A number of nutrient media suitable for plant tissue culture, each containing a distinctive composition of carbon source, salts, minerals and vitamins, are known in the art. Among those which are suitable as the basal medium are B5 (Gamborg et al. *Exp. Cell Res.* 50:151-158, 1968), White's (White, *A Handbook of Plant and Animal Tissue Culture,* Jaques Cattel Press, Lancaster, PA, 1963) and SH (Schenk and Hildebrandt, *Can. J. Bot.* 56:166-204, 1962). Preferred for the culture procedure, however, is MS medium (Murashige and Skoog, *Physiol. Plant.* 15:473-497, 1962), or B5 medium.

Variation in regenerated plants is frequently observed when an explant is grown on a medium containing at least one auxin, and, preferably, at least one auxin and at least one cytokinin. Auxins which may be used in the present method include indole acetic acid (IAA), indole butyric acid (IBA), naphthalene acetic acid (NAA), and 2,4-dichlorophenoxyacetic acid (2,4-D), with 2,4-D being the preferred auxin. The effective range of auxin concentration is about 2.0-9.0 $\mu$M, with about 2.25-4.0 $\mu$M being a preferred range when 2,4-D is employed. Other auxins may be substituted for 2,4-D, but concentrations necessary to achieve an equivalent biological effect are generally higher. The presence of a cytokinin in the medium is typically preferred. Among the known cytokinins are 6-benzyladenine (6-BA), zeatin, kinetin, and 2-isopentyladenine (2-iP). The preferred cytokinin in this method is 6-BA. The range of concentration of cytokinin in the present medium may be from 0-20 $\mu$M, with about 10 $\mu$M being a preferred concentration when 6-BA is used.

To initiate callus proliferation, an explant, e.g., petiole, is cut into about 1 cm sections, and placed into the selected medium with an appropriate hormonal concentration.

Callus initiation in celery can be slow, and it may be as long as a month before any substantial amount of tissue proliferation, independent of the plant, is recoverable. When callus does appear, it is generally the hard green callus, rather than friable callus, which is best suited for embryo production. Suitable callus is selected and transferred to an embryogenic medium containing no growth regulators. These cultures are subcultured every month or so onto fresh embryogenic medium of the same composition. Embryos first appear about 8 weeks after inoculation and plantlets are recoverable usually after about 3-4 months.

Population Selection

IN order to develop a line having agronomically acceptable properties, mature individual $R_o$ plants were outcrossed to adjacent $R_o$ plants. Seed was then collected and vernalized. The vernalized seed was planted in replicated field trials, along with the progenitor pascal celery check varieties. Experimental lines were then evaluated at typical harvest maturity for improvement over the parental line in the processing characteristic of choice. In small scale evaluations, damaged and overmature outer petioles were removed from the plant, and starting at 1.5 inches from the base, successive transverse cuts were made at 3 inch intervals. To assist in identification of lines having potential for improved efficiency of conversion to finished product, a numerical parameter for "Stick Yield" (SY) was devised. SY was calculated by first determining the gross fresh weight of a random sample of at least ten celery plants, and subsequently deriving sticks which conform to the physical characteristics as described in U.S. Pat. No. 4,711,789 which have been determined to be useful for a suitable final packaged product. Those sticks not conforming with these characteristics are discarded or used for other purposes. The conforming selected sticks are used in evaluation of SY. SY is calculated as the quotient of selected stick weight divided by the gross sample weight.

Those lines which consistently produce the highest SY (and thus the highest processing conversion efficiency) are then propagated by sowing their seed in flats and growing 60-80 days, or until 7-8 true leaves have emerged. The for plants are then vernalized and transplanted to a dry mild climate. When plants begin to bolt, 25% of the population which flowered the fastest was eliminated. Mature seed was then harvested and stored under conditions of low humidity and temperature.

ditions, callus generally formed within a month from explanting. The best callus for continuation into embryogenesis was typically not friable, but rather hard and green.

Embryogenesis

Callus was removed from the proliferation medium, and spread on embryogenic media comprising MS or B5 salts and vitamins, 3% sucrose, and 0.9% agar at pH 5.7 in 4 ounce tissue culture bottles. The bottles were covered with clear, presterilized plastic to permit gas exchange and maximum light exposure. The embryogenic cultures were subcultured every month into fresh media of the same composition. These cultures were incubated at 25°-27° C. under 16 hour days on culture racks equipped with photosynthetic lights. Plantlets, which were ready for transplant into soil, were recovered after approximately 3-4 months.

When plantlets were 5-15 cm in height and had de-

TABLE 1

| | COMPARISON OF STICK YIELDS AND SENSORY EVALUATION | | | | | | | |
|---|---|---|---|---|---|---|---|---|
| | YEAR 1 | | | | YEAR 2 | | | |
| | Oxnard | Santa Maria | Chualar | Watsonville | Watsonville | Willa-mette | Santa Maria | Watsonville |
| Stick Yield (%) | | | | | | | | |
| 201 | 41.20 ± 4.16 | 25.82 ± 1.69 | 29.7 ± 0.77 | 33.90 | 46.16 ± 3.51 | 30.94 | 32.90 ± 2.95 | 31.00 ± 2.95 |
| 331 | 46.90 ± 1.73 | 31.11 ± 5.52 | 47.95 ± 4.9 | 38.00 | 51.75 ± 3.28 | 42.31 | 41.83 ± 3.23 | 40.50 ± 4.23 |
| t statistic = 5.24; significant difference at 99%; $\alpha_{(0.01,7)}$ = 3.00 | | | | | | | | |
| Sensory Score | | | | | | | | |
| 201 | 5.00 | 5.00 | 3.50 | 5.50 | 3.88 ± 0.63 | 2.00 | 5.00 ± 0.50 | 3.50 ± 1.22 |
| 331 | 4.50 | 4.50 | 4.00 | 3.50 | 1.83 ± 0.76 | 3.00 | 4.63 ± 0.48 | 4.63 ± 0.75 |
| t statistic = 0.93; no significant difference $\alpha_{(0.10,7)}$ = 1.41 | | | | | | | | |

5. EXAMPLES

Somaclonal Variation

Propagation of Donor Plants

Seed of DNAP line 201 was sown in one-inch flats containing Metromix 215, and germinated in the greenhouse. The celery seedlings grew to a height of approximately 10-15 cm over a period of two months. At this stage, the plants were used for initiating tissue cultures. Following the initial cutting, plants could be reused for tissue culture for up to six months as they generated new petioles.

Cell Culture

Young petioles (about 2 months) were harvested by cutting the plants 1-2 cm above the base. The tops of the petioles were then cut just below the most proximal leaves and surface sterilized in a 20% Clorox solution containing a drop of liquid detergent for 15-20 minutes on an orbital shaker. The petioles were then rinsed three times with 300-500 ml of sterile distilled water to remove Clorox.

After rinsing, the petioles were then cut into pieces 5-7 mm long and split three quarters of the way along the longitudinal axis and placed on the proliferation medium, to provide maximum surface area exposure. The proliferation medium comprised either MS or B5 salts and vitamins, 3% sucrose, and 0.09% agar at pH 5.7, in a sterile petri dish. The medium contained the growth regulators 2,4-D and 6-BA, in amounts of 2.25 $\mu$M and 10 $\mu$M, respectively. Explants were incubated at 25°-27° C. under 16 hour days on growth racks equipped with photosynthetic lights. Under these conveloped sufficient root systems, they were transplanted into soil (Metromix 215) in Magenta boxes. The boxes were covered with clear plastic to prevent moisture loss; over time the plastic was rolled back to facilitate acclimation of the plants to ambient environmental conditions. This process generally took 1-2 months. Hardened-off plants were then moved to the greenhouse to permit the plants to grow and develop a good root system. Plants were vernalized for 2-3 months, with 10 weeks being optimal, at 8°-10° C. Supplemental lights were provided to produce 10-12 hour daylengths. Following vernalization, plants would begin to flower within 1-2 months. Flowering generally continued for 2-3 months.

Screening For Somaclonal Variants

Individual $R_o$ plants produced by the method outlined above are outcrossed to adjacent $R_o$ plants. The seed produced are collected and vernalized; the vernalized seed were planted in replicated (>3) trials with the progenitor pascal celery check varieties. The experimental lines which had the highest processing conversion efficiency in terms of SY are selected for further propagation.

The selected improved lies are propagated by selfing. Seeds are sown in a molded plastic or styrofoam flat, and grown from 60-80 days or until 7-8 true leaves emerge. The plants are vernalized at 10° C. for 21 days, then transplanted in an area with a dry, mild climate at least one kilometer from other flowering celery at a density of 10,000 plants per acre. When plants begin to bolt, 25% of the population which flowers the fastest are eliminated. Mature seed is then harvested from the remaining plants, then milled and stored under conditions of low temperature and humidity which typically prolong seed viability until use.

Selected Lines

Utilizing the procedures on outlined above, the novel variety DNAP-331 has been developed. Earlier trial and selection efforts on a line of the pascal celery variety Tall Utah produced a line designated DNAP-201. This line was chosen as the variety exhibiting the highest degree of consumer preference from the standpoint of flavor and texture. Sensory evaluation of 201 in comparison with commercially available celery were conducted with 750 consumers, who showed significant preference for 201. This variety was preferable as "better tasting", "sweeter" and "less stringy."

The 201 variety was then subjected to a program of somaclonal variation as outlined above, in an attempt to produce variants having improved processing characteristics over the parent variety. In particular, the somaclones were screened for plants producing longer, thinner petioles, thereby potentially increasing stick yield. Then consecutive plants were prepared as they would be in a standard celery harvest. After taking quality notes, these were cut in a device which emulates the process described in U.S. Pat. No. 4,751,094. Acceptable sticks were sorted, weighed and classified according to SY by the formula noted in Section 4.2, supra. Selfed and outcrossed seed of several hundred somaclones was sown into trials, and from these trials the line designated DNAP-331 has emerged as consistently at least about 25% greater stick yield than the 201 line.

The two lines were compared for sensory qualities according to the following procedure:

Celery stalks were stripped and outer petioles and hearts discarded. The remaining petioles were cut into three inch sticks, discarding flared ends and knuckles. A special quantitative descriptive analysis procedure (Laboratory Methods for Sensory Evaluation of Food. Canadian Government Publishing Center, Ottawa, Canada pp. 48-50, 1977) was developed for evaluation of snacking celery. Coded, randomly presented samples were evaluated for appearance, flavor and texture, as well as overall acceptability by trained expert panelists. All ratings were done on a scale of 1 (lowest) to 9 (highest). In addition to rating the sample for each individual attribute, the panelist was also asked to provide a single rating of the overall acceptability of the material relative to all the evaluation criteria. Specific characteristics which were evaluated include color, hollow, intensity, bitterness, sweetness, saltiness, stringiness, juiciness, crunch, tenderness and crispness.

A tabular comparison of line 331 with line 201, for both stick yield and sensory quality, is found in Table 1. The figures clearly show a significant difference in stick yield between the 201 and 331 lines, while showing no significant difference in sensory qualities, even when grown over a variety of locations.

Seeds of the variety DNAP 331 have been deposited with the American Type Culture Collection assigned accession number ATCC 40621.

What is claimed is:

1. A celery plant having all of the characteristics of a plant produced by seed deposited with the American Type Culture Collection and assigned accession number 40621, and progeny, clones, and somaclones having all of said characteristics thereof.

2. Seed-deposited with the American Type Culture Collection and assigned accession number 40621.

3. A regenerable tissue culture of the plant of claim 1.

* * * * *